(12) United States Patent
Casalino et al.

(10) Patent No.: US 12,167,890 B2
(45) Date of Patent: *Dec. 17, 2024

(54) LASER DEVICE FOR DERMOCOSMETIC TREATMENTS AND TRACING KIT

(71) Applicant: BIOS S.R.L., Milan (IT)

(72) Inventors: Aldo Casalino, Vimodrone (IT); Lorenzo Casalino, Vimodrone (IT)

(73) Assignee: BIOS SRL, Milan (IT)

( * ) Notice: Subject to any disclaimer, the term of this patent is extended or adjusted under 35 U.S.C. 154(b) by 31 days.

This patent is subject to a terminal disclaimer.

(21) Appl. No.: 17/728,287

(22) Filed: Apr. 25, 2022

(65) Prior Publication Data

US 2022/0265349 A1 Aug. 25, 2022

Related U.S. Application Data

(63) Continuation of application No. 16/914,379, filed on Jun. 28, 2020, now Pat. No. 11,337,759, which is a
(Continued)

(30) Foreign Application Priority Data

Oct. 8, 2014 (IT) ............ MI2014A001759
Oct. 5, 2015 (IT) .......... 102015000058198

(51) Int. Cl.
*A61B 18/20* (2006.01)
*A61B 18/00* (2006.01)
(Continued)

(52) U.S. Cl.
CPC .......... *A61B 18/203* (2013.01); *A61B 90/361* (2016.02); *A61B 90/37* (2016.02);
(Continued)

(58) Field of Classification Search
CPC ..... A61B 18/203; A61B 90/361; A61B 90/37; A61B 2090/3614; A61B 2018/20357;
(Continued)

(56) References Cited

U.S. PATENT DOCUMENTS 6,360,658 B1  3/2002  Benson
6,406,474 B1*  6/2002  Neuberger ........... A61C 19/066
                                                            606/9
(Continued)

FOREIGN PATENT DOCUMENTS

EP     1796569    6/2007
WO     0123032    4/2001
(Continued)

OTHER PUBLICATIONS

R.G. Wheland, "Laser-Assisted Hair Removal", Lasers in Dermatology, vol. 15, pp. 469-477.
Italian Search Report dated Jun. 2, 2015.

*Primary Examiner* — Alyssa M Alter
*Assistant Examiner* — Jessandra F Hough
(74) *Attorney, Agent, or Firm* — ISUS INTELLECTUAL PROPERTY PLLC; Anthony Jason Mirabito

(57) ABSTRACT

A method of dermocosmetic treatment for skin tissue includes a plurality of treatment laser light sources which are in communication with a rectangular-shaped optical fiber; the optical fiber includes a proximal end to receive laser light from the plurality of treatment laser light sources and a distal end to transmit overlapping laser light to the area of skin tissue to be treated; the plurality of treatment of laser light sources are activated to impinge one or more rectangular-shaped laser light images within one or more rectangular-shaped areas.

9 Claims, 4 Drawing Sheets

Related U.S. Application Data continuation of application No. 16/189,543, filed on Nov. 13, 2018, now Pat. No. 10,722,307, which is a continuation of application No. 14/878,130, filed on Oct. 8, 2015, now abandoned.

(51) Int. Cl.
  *A61B 18/22* (2006.01)
  *A61B 90/00* (2016.01)
  *A61N 5/06* (2006.01)

(52) U.S. Cl.
  CPC ......... *A61N 5/0616* (2013.01); *A61N 5/0617* (2013.01); *A61B 2018/00452* (2013.01); *A61B 2018/00458* (2013.01); *A61B 2018/0047* (2013.01); *A61B 2018/00476* (2013.01); *A61B 2018/20357* (2017.05); *A61B 2018/20359* (2017.05); *A61B 2018/2205* (2013.01); *A61B 2018/2244* (2013.01); *A61B 2018/2255* (2013.01); *A61B 2018/2266* (2013.01); *A61B 2090/3614* (2016.02)

(58) Field of Classification Search
  CPC ........... A61B 2018/20359; A61B 2018/00452; A61B 2018/00458; A61B 2018/0047; A61B 2018/00476; A61B 2018/2205; A61B 2018/2244; A61B 2018/2255; A61B 2018/2266; A61N 5/0616; A61N 5/0617
  See application file for complete search history.

(56) References Cited

U.S. PATENT DOCUMENTS

| | | | |
|---|---|---|---|
| 6,413,268 | B1 | 7/2002 | Hartman |
| 6,682,524 | B1 | 1/2004 | Jens et al. |
| 6,758,845 | B1 | 7/2004 | Weckwerth et al. |
| 8,246,611 | B2 | 8/2012 | Paithanker |
| 2002/0107509 | A1 | 8/2002 | Neuberger |
| 2002/0123781 | A1 | 9/2002 | Shanks |
| 2002/0138119 | A1* | 9/2002 | Angeley ............ A61B 18/203 606/9 |
| 2002/0183811 | A1* | 12/2002 | Irwin .................. A61N 5/0616 607/94 |
| 2005/0154382 | A1* | 7/2005 | Altshuler ............... A61B 90/30 606/9 |
| 2006/0293728 | A1* | 12/2006 | Roersma ............ A61N 5/0617 607/88 |
| 2007/0116607 | A1 | 5/2007 | Wang |
| 2008/0082089 | A1* | 4/2008 | Jones .................. A61N 5/0616 606/9 |
| 2009/0326523 | A1 | 12/2009 | Lazarev |
| 2010/0049180 | A1 | 2/2010 | Wells |
| 2010/0150878 | A1 | 6/2010 | Bellomo |
| 2016/0015995 | A1* | 1/2016 | Leung .................. A61N 2/006 600/14 |

FOREIGN PATENT DOCUMENTS

| | | |
|---|---|---|
| WO | 0126573 | 4/2001 |
| WO | 02076318 | 10/2002 |
| WO | 2004075718 | 9/2004 |
| WO | 2006089227 | 8/2006 |

\* cited by examiner

LASER DEVICE FOR DERMOCOSMETIC TREATMENTS AND TRACING KIT

RELATED APPLICATIONS

This application is a continuation of U.S. application Ser. No. 16/914,379, filed Jun. 28, 2020, which is a continuation of U.S. application Ser. No. 16/189,543, filed Nov. 13, 2018, now U.S. Pat. No. 10,722,307, issued on Jul. 28, 2020, which is a continuation of U.S. application Ser. No. 14/878,130, filed Oct. 8, 2015, now abandoned, which claims priority to Italy Application No. 102015000058198, filed Oct. 5, 2015 and Italy Application No. MI2014A001759, filed Oct. 18, 2014.

BACKGROUND OF THE PRESENT INVENTION

Today, laser technology is widely used in dermatologic, aesthetic medicine, and professional aesthetic treatments. The laser removal of hair is one among the possible treatments, one of the most widely used worldwide. The concept on which it is based is selective photothermolysis. By selecting a laser with the proper wavelength and energy per surface unit (fluency), a particular target substance present in the light-absorbing tissue (chromophore), such as, for example, melanin or hemoglobin, absorbs the laser beam energy so as to be heated such that the function of the tissue containing the chromophore is destroyed. The tissues which are present in the same area which do not have a high concentration of target chromophore will be not affected. For example, during epilation, a laser emits a monochromatic light at a predetermined fluency, so as to selectively hit the melanin present in the hair bulb, thus destroying it (R. G. Wheland, "Laser-assisted hair removal", Lasers in Dermatology, Vol. 15, pp. 469-477). Hair are composed of two major parts: the shaft, i.e., the hair portion above the epidermis, and the root, that is the portion below the epidermis surface. Various tissues surround the hair roots. The hair color is mainly due to the presence of melanin. Melanin is produced at the base of the hair follicle. It is exactly the presence of melanin that made the use of the laser for the epilation possible, where melanin acts as a target chromophore and, since it is located at the base of the hair follicle, with the heating due to the laser it damages the hair follicle itself.

Other dermatologic and aesthetic medicine treatments in which the laser technology finds wide application are the face and body vascular treatments, among which, by way of non-exhaustive example, the removal of telangectasias, erythroses, red and blue capillaries, angiomas, varicose veins are noted; treatments of face and body pigmented lesions, among which, by way of non-exhaustive example, removal of tattoos, skin stains, melasmas, melanomas, skin moles; resurfacing, non-ablative or ablative photorejuvenation treatments, peeling, dermatologic treatment of skin imperfections to be treated surgically and non-surgically, for example, the treatment of scars in general, including post-acne scars, keloids, condylomata, fibromas; the treatments of psoriasis and vitiligo are noted.

Among the various classes of lasers that are used, i) diode lasers; ii) lamp-pumped lasers are distinguished.

In diode lasers, the source is composed of power emitting diodes that are assembled to one another to form a diode block, so-called stacks, so as to obtain a high overall power, currently up to 4,000 W. This energy is emitted with a very high divergence, and it is generally collected by "optical funnels", i.e., light guides collecting the energy and transporting it onto a small, generally rectangular area. These guides are usually of sapphire.

In the lamp-pumped lasers, a crystal rod, referred to as an active medium, is excited by a lamp with short, intense pulses, thus emitting energy for the time corresponding to the turn-on period of the lamp. The lamp-pumped lasers do not emit continuously, as the case is instead for the diode laser, but with pulses having a peak power up to some GWs and with a duration of the order of milliseconds, microseconds, or even nanoseconds. In the lamp-pumped systems, the laser beam emitted by the crystal is conveyed with a lens system in an optical fibre which has the function of transporting the energy. The use of fibers allows the operator working also at a distance of meters from the source, without particular losses of energy during transportation. In some cases, when the source is inserted in a handpiece, the energy is transported also by light guides, but with a high dispersion of energy and a worsening of the quality of the beam.

The optical fibres currently used in the laser systems applied to dermocosmesis, medicine, and aesthetic treatments are optical fibres having a circular section, typically coupled to a handpiece projecting in output the image located at the inlet of the handpiece, so that the dimension of the image in output can be adjusted by the user. Circular images in input will result in output images which are again circular, but of different dimensions.

During the treatment, it is necessary to expose to the energy laser in a complete and even manner the area of tissue at issue, and the circular shape of the image in output is a major obstacole. Circular-shaped spots arranged side by side cannot allow a complete covering of the area of interest without being superimposed. The superimposition creates energy overexposures, with the consequent risk of burns. Having to avoid the superimposition, it is inevitable that there are untreated, uncovered areas, which require a further treatment to be performed in a successive moment.

A further drawback deriving from the use of circular-shaped spots is the fact that the energy is distributed in a Gaussian manner onto the circular spot, with a maximum intensity peak at the centre of the area. These localized densities increase the risk of undesired microburns at the centre of the spot, and make the energy on the perimeter of the spot itself insufficient.

The need is strongly felt, to provide devices for dermocosmetic, medical, or aesthetic laser treatments which allow an homogeneous treatment of the area to be treated, avoiding the risks related to superimpositions and to areas in which a higher density of energy is concentrated, in addition to the drawbacks related to the failed treatment of some areas.

SUMMARY OF THE PRESENT INVENTION

In an aspect, a method of dermocosmetic treatment for skin tissue includes:
providing an area of the skin tissue to be treated; providing a plurality of treatment laser light sources, the laser light sources each being in communication with a rectangular-shaped optical fiber, the optical fiber having a proximal end to receive laser light from the plurality of treatment laser light sources and a distal end to transmit overlapping laser light to the area of skin tissue to be treated; and activating the plurality of treatment of laser light sources to impinge one or more rectangular-shaped laser light images within one or more rectangular-shaped areas.

In another aspect, the method includes the step of adjusting the size of the produced rectangular-shaped images on the area of the skin tissue.

In yet another aspect, the method further includes a handpiece, the handpiece containing at least the distal end of the optical fiber, the handpiece further comprising one or more sensors, the one or more sensors sensing the position of the handpiece with respect to contact with the skin tissue are to be treated. The one or more sensors sense the position of the one or more sensors over the one or more rectangular-shaped areas and communicating the position to a laser emission control system.

In yet a further aspect, the method further includes the step of the one or more sensors providing synchronization signals to the laser emission control system to activate the plurality of laser light sources when the handpiece is aligned with each one of the one or more rectangular-shaped areas on the area of the skin tissue to be treated.

In an aspect, the optical fiber has a square-shaped core for producing a square-shaped image when activated, and further, the plurality of treatment laser light sources comprises two laser sources having different wavelengths, further comprising the step of activating the two laser sources simultaneously. The two laser sources are a neodymium-YAG rod and an Alexandrite rod.

It is the object of the present invention a device for dermocosmetic, medical, or aesthetic laser treatments, comprising:
A) a laser system comprising a lamp-pumped source;
B) an optical fibre;
C) a handpiece or a scanner connected to said optical fibre, comprising a lens and mirror system projecting the image of the laser beam onto the area to be treated;
characterized in that said optical fibre has a rectangular section and said image onto the area to be treated is rectangular.

It is a further object of the present invention a tracing kit that allows the marking of a surface area, preferably of biological tissue, with a fluorescent or photosensitive substance invisible to light. Such an invisible and fluorescent or photosensitive substance absorbs the electromagnetic radiation with the proper wavelength emitted by the illuminator and reflects it in the visible spectrum.

The meaning given to some terms in the context of the present invention is set forth herein below.

By spot is meant the area of the tissue on which the laser acts instant by instant, also defined as the image of the laser beam onto the area to be treated.

By fibre with a rectangular section and, consequently, by rectangular image onto the area to be treated, as it shall be apparent to those skilled in the art, is meant a section and/or an image the vertices of which can be acute or rounded, with a curvature radius ranging from 0 to 300 micrometers, preferably 50 to 200 micrometers.

By handpiece is meant an optical system receiving the image in output from an optical fibre and projecting onto the area to be treated. The handpiece can be with a stationary or variable focus. In the first case, the lens system therein is stationary, and the image projected onto the tissue has a fixed dimension. In the second case, the lens system inside the handpiece is mobile, since one or more lenses slide by a manual or automatic sleeve, and the operator can change the spot dimension.

By scanner is meant herein an electronic device connected to an optical fibre, which distributes in an area defined by the operator the laser pulses in a quick and automatic manner, according to a sequential or random emission pattern. The emitted spots fill the area defined by the operator, which is in a so-called fractionated area, i.e., in an area treated by many thin pulses arranged in a random or sequential manner inside thereof.

DETAILED DESCRIPTION OF THE PRESENT INVENTION

Figure 4:
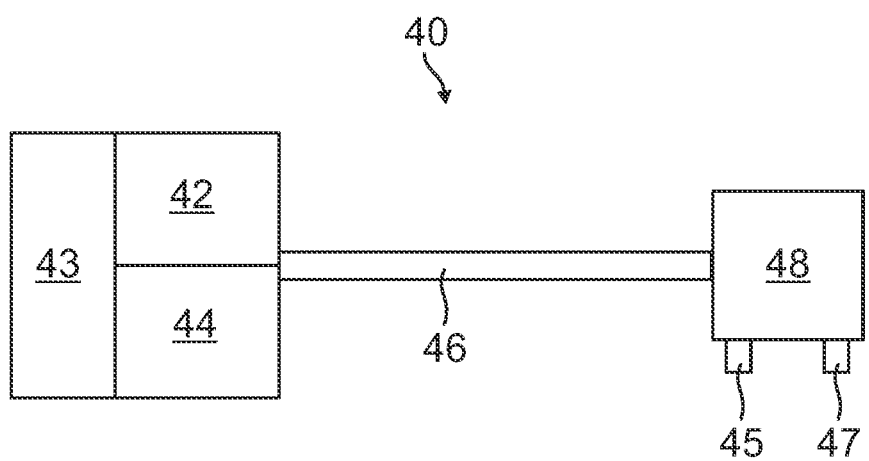
FIG. 4: embodiment of the optical system of the present invention.
Figure 5:
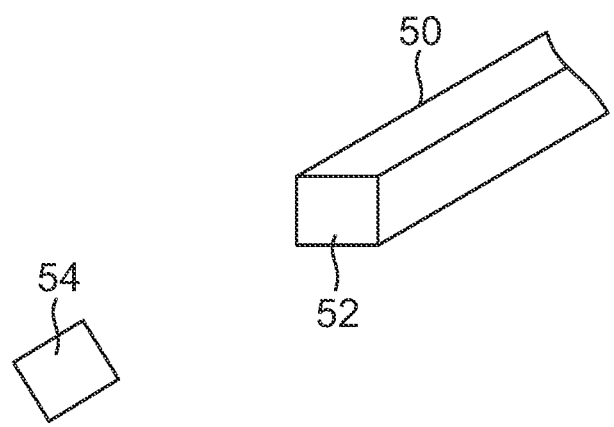
FIG. 5: embodiment of a rectangular cross-section optical fiber.

It is an object of the present invention a device for dermocosmetic, medical, or aesthetic laser treatments, comprising:
A) a laser system 40 comprising a lamp-pumped source (FIG. 4);
B) an optical fibre (FIGS. 4 and 5);
C) a handpiece or a scanner connected to said optical fibre, comprising a lens and mirror system projecting the image of the laser beam onto the area to be treated (FIG. 4);
characterized in that said optical fibre 50 has a rectangular section and said image is rectangular (FIG. 5).

The lamp-pumped laser source of the present invention emits a Gaussian laser beam having a circular section and it emits with wavelengths ranging between 700 and 2,200 nm. In a solution where the active medium is an alexandrite crystal (rod) 42, the wavelength is mainly of about 755 nm 44. In an alternative solution, where a neodymium-YAG crystal is used, the wavelength is about 1,064 nm. In a further solution, where the crystal is a thulium crystal, the wavelength ranges from 1,900 to 2,000 nm, while if the crystal is a holmium crystal, the wavelength ranges in the neighborhood of 2,100 nm. The sources in the laser systems will be able to be more than one in the same system and they will be able to emit singularly or in a mixed or sequential manner. Preferably, where the device is for laser epilation, said rod 46 is an alexandrite and neodymium-YAG rod, with a single emission, mixed in the same fibre, or sequential, i.e., an emission of pulses by the first source, followed by pulses emitted by the second source.

The laser source preferably operates with frequencies ranging between 0.33 Hz and 5 Hz.

In a preferred embodiment, the optical fibre transporting the energy produced by said laser source is a squared-section optical fibre.

Said optical fibre is naked or sheathed for due protection and it has a side dimension ranging between 100 micrometers and 2.5 mm.

Said handpiece or scanner of the present invention are characterized in that they project a rectangular spot onto the area to be treated.

In a preferred embodiment, said handpiece or scanner 48 receives a squared image from a squared optical fibre, thus projecting a squared spot 54 onto the area to be treated.

It shall be apparent to those skilled in the art that by squared optical fibre 50 and squared spot 54 is meant a section, and consequently an image that is squared in the equal and opposite sides, and the vertices of which can be acute or rounded.

For comparison purposes, a device comprising an optical fibre having a circular, not rectangular, section, as it is instead in the inventive solution proposed is also described herein. In this case, a light guide or a diaphragm is arranged within the optical system of the handpiece, preferably in a cube, parallelepiped, or truncated pyramid shape, which allows the output of a circular image when the light beam in input is circular. An apparent drawback of this embodiment is to be found in the considerable loss of energy due to the necessary presence of a light guide.

Optionally, said handpiece is provided with sensors 45, 47 which are rested onto the area to be treated and which, by sliding onto the area to be treated with the displacement of the handpiece by the operator, send position signals to the laser emission control system 43, so as to synchronize the emission frequency of the laser pulse with the position, in order to emit perfectly adjacent spots, without superimposition and without untreated areas. By way of example only, where the spot is a square with side 2 cm long, every 2-cm displacement of the handpiece recorded by the sensor will send to the source the signal for an emission. Again, with a squared spot with side 2 cm long, where the displacement rate doubles, the source will emit the double the emissions, while keeping the time units constant. By way of example only, the sensors optionally used in the present invention are of the type described in U.S. Pat. No. 6,758,845.

Since said sensors directly contact the area to be treated, said sensors are disposable, or they are easily sterilizable.

Optionally, said device comprises a spacer, whereby spacer is meant a rectangular ring applied onto the outlet of said handpiece. Said ring will have a side dimension larger than that of rectangular the spot, and a suitable height to properly space apart the area to be treated from the focusing lens present in said device, where said height is about 40 mm.

In a further embodiment, herein described by way of comparison purpose, where said device leads to circular images in output from the handpiece, said circular image is made rectangular by applying, to the output of said handpiece, a spacer which is a rectangular ring diaphragm, where said image circular in output has a diameter larger than the opening of said rectangular ring, and the walls of said rectangular ring have such a thickness as to circumscribe the circular image in output from the handpiece in the area defined by the opening of said rectangular ring.

This solution involves a considerable loss of energy, since part of it, in particular, the portion exceeding the opening of the rectangular ring, is necessarily lost, since it does not hit the area to be treated, but it is blocked by the edge of said rectangular ring. A second problem, closely related to the previous one, is due to the overheating of the rectangular ring, with risk of burns.

Surprisingly, the solution of the present invention is capable of solving these problems. Further advantages of the device of the present invention are set forth herein below.

Said invention also relates to a method of dermocosmetic treatment, where said method comprises:
  A. providing an area to be treated, where said area is a portion of skin of a subject who wants said treatment;
  B. exposing said area to a laser light 41 source at a wavelength ranging between 700 and 2.200 nm, where said area is hit by a rectangular spot in which the energy is distributed in a homogeneous, even manner on the entire area of the spot;
  C. repeating the step in B until said area to be treated is completely treated by said rectangular spots.

In a preferred embodiment, said area to be treated is hit by a series of squared spots emitted in a sequence side by side to one another.

Figure 1:
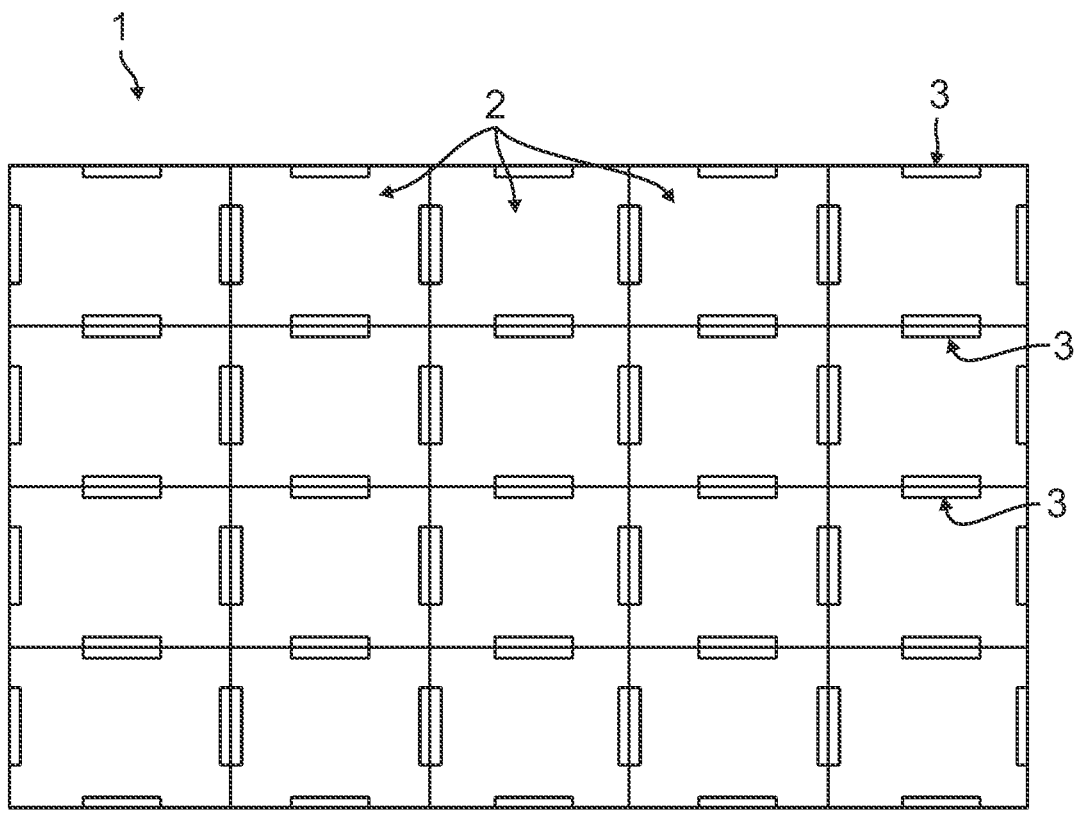
FIG. 1: example of a pattern with slits for the definition of the area to be treated.

In a further aspect, the present invention relates to a slit pattern. By way of example only, a slit pattern is set forth in FIG. 1, patterns describing different geometries from those exemplified in FIG. 1 are to be meant as encompassed herein. Said slit pattern (1) is a flexible, planar surface, preferably of colored plastic, on which the pattern of the area to be treated is drawn, divided into rectangular sections (2), where each section represents the area that is hit by a single spot. Said sections are mutually defined on said planar surface by slits (3).

Optionally, said method also comprises, before said step A, a step A' where said slit pattern is arranged onto the area to be treated and a marker is distributed thereon, so that said marker draws onto the area to be treated the same pattern represented by the slits (3) on the slit pattern (1).

In a preferred embodiment, a biocompatible liquid invisible to the naked eye and fluorescent when lighted by UV light is distributed onto said slit pattern located onto the area to be treated. In this embodiment, the handpiece has UV emitting LEDs. Alternatively, said marker is a liquid which, when irradiated by the laser wavelength, from transparent turns colored, hence visible to the operator.

Once the slit pattern has been lifted, it is proceeded with the described method, and the operator is able to see in a clear manner the area to be treated by virtue of the UV light, which makes the pattern visible also where the operator uses laser light protection glasses. The displacement of the handpiece, especially if a rectangular ring spacer is associated thereto, mirroring the geometrical shape of the sections drawn by said slit pattern, is facilitated by the pattern, making the displacement of the handpiece from a section to the next one practical.

It is a further object of the present invention a marking kit that comprises:
  a marking instrument, which is preferably a pad stamp or roller stamp (101);
  an ink invisible and photosensitive or fluorescent to the electromagnetic radiation with the proper wavelength, such as, by way of non-exhaustive example, the wavelength in the UV or IR range;
  at least one illuminator which emits electromagnetic radiation at said proper wavelength, by way of non-exhaustive example light bulbs, neon, LEDs or lasers;
  at least one support for said illuminator, by way of non-exhaustive example a handpiece, spectacles, panels, lamps or fixtures on a stand or wall or ceiling.

Figure 2:
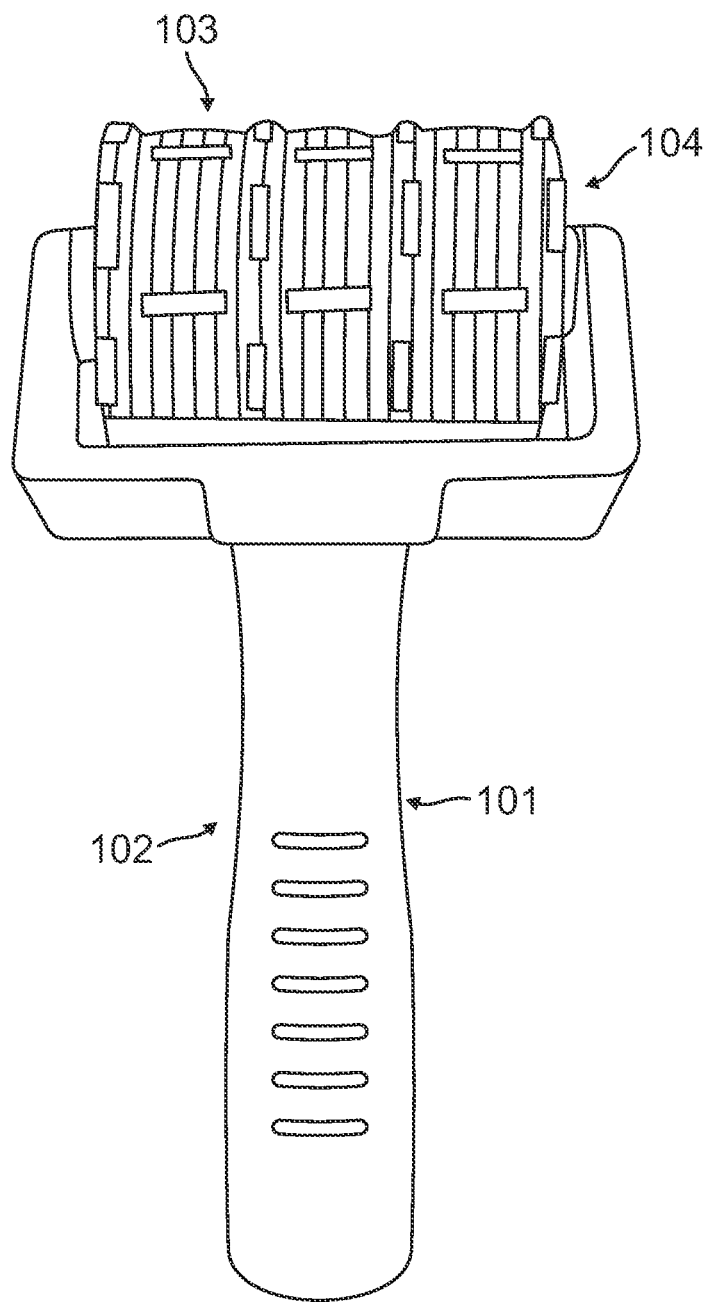
FIG. 2: roller stamp of the present invention.

Said marking instrument, which is preferably a roller stamp (101), has the pattern chosen for said marking. FIG. 2 shows a preferred embodiment of the said roller stamp. Said roller stamp (101) comprises a handle (102), which supports a roller (103). Said roller (103) has a pattern in relief. In the embodiment in FIG. 2, said pattern consists of segments (104) arranged on said roller so as to form a contiguous square pattern (105) as a whole. In alternative embodiments, all belonging to the scope of application of the present invention, said pattern consists of alternative geometric shapes, e.g., circles having equal or different diameter or rectangles.

Said invisible and fluorescent or photosensitive ink is a biocompatible substance, e.g., chosen from those known for cosmetic use. Said ink is apt to persist on the tissue after having been applied, also during the dragging of other objects on it, such as for example treatment application handpiece, in order not to distort the marking. Following a radiation with electromagnetic radiations with the proper wavelength, said substance becomes visible. In a preferred embodiment, said ink is water-based, invisible and emits fluorescence in the visible spectrum if radiated with UV light.

Said illuminator is preferably chosen from the group that comprises a halogen bulb, a gas neon, a LED, a laser. In a preferred embodiment, said illuminator is a LED that emits in the UV spectrum.

Said illuminator is supported by a stand which supports a bulb or LED light, or is fitted on a neon ceiling light, or is present on the handpiece used for the treatment, or in a preferred embodiment is mounted on spectacles worn by the operator.

Figure 3:
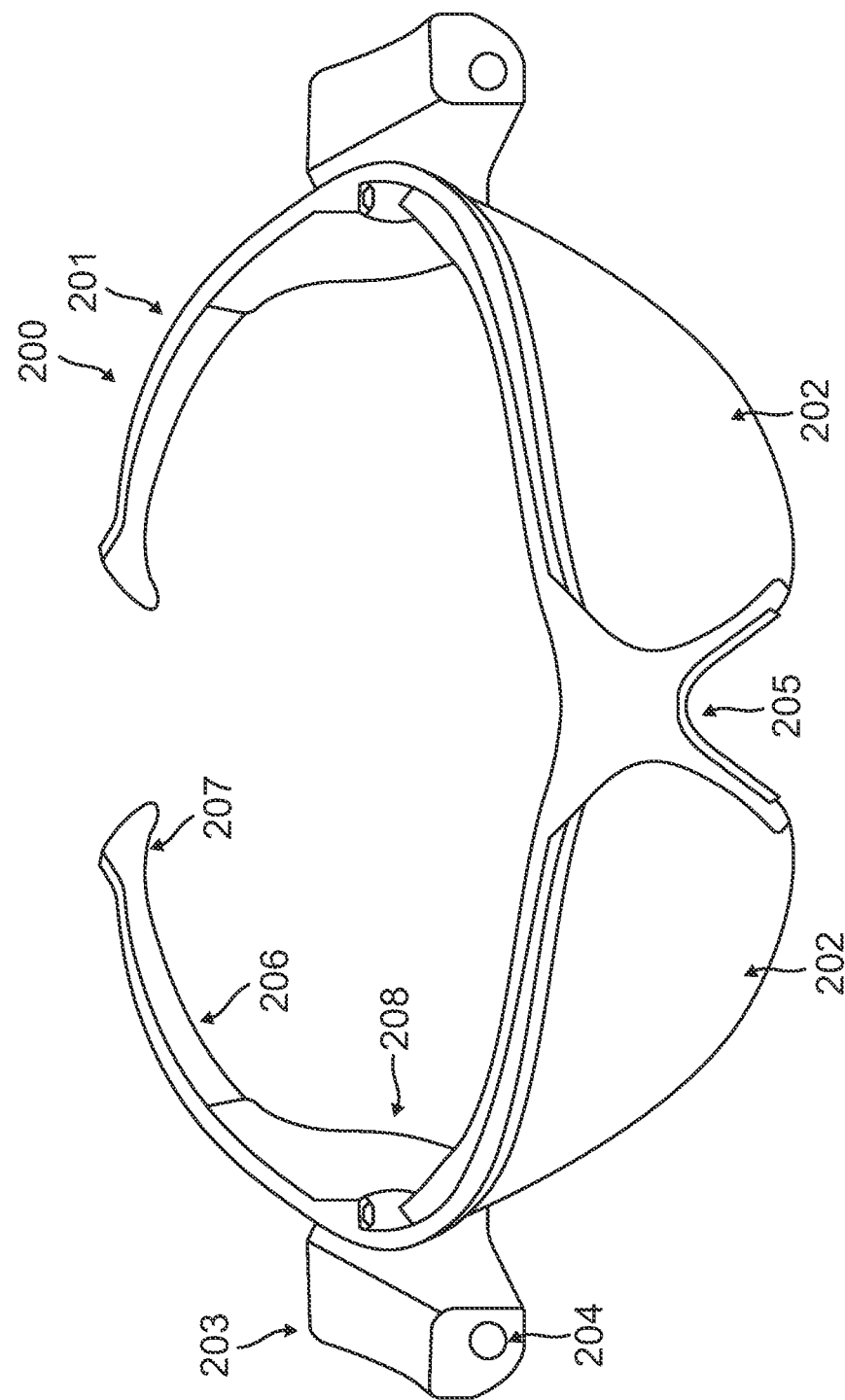
FIG. 3: spectacles with LED according to the present invention.

Said illuminator mounted on spectacles is preferably of the LED type and an embodiment thereof is shown in FIG. 3. Said spectacles (200) comprise a frame (201) and two lenses (202). Said frame (201) comprises a frontal support portion for said lenses, centrally separated by a nosepiece (205) and two sidepieces (206) for positioning it on the operator. Each of said sidepieces (206) has a distal portion (207), which is arranged on the ear of said spectacle wearer who is the operator, and a proximal portion (208), which is joined to the frontal frame portion that supports the lenses. At least one support (203) for at least one LED (204) is hooked on the frame (201) of said spectacles (200) or on the lenses (202). In one embodiment, said at least one support (203) is positioned frontally on said frame, over the nosepiece (205) of said spectacles (200). In a further embodiment, it is positioned laterally on the proximal portion (208) of said sidepiece (206). In a further embodiment, said support is positioned frontally on said frame, in outer lateral position, near the joining point between said frontal portion and said sidepiece. In a preferred embodiment, said frame comprises two supports and, even more preferably, said two supports (203) are positioned on the proximal portion (208) of said two sidepieces (206).

It is a further object of the present invention a method for marking surface areas.

Said method comprises:
a) providing a surface area;
b) providing a kit according to the present invention comprising a marker which is preferably a roller stamp, an ink invisible and photosensitive or fluorescent to the electromagnetic radiation with the proper wavelength, at least one illuminator positioned on at least one support, wherein said illuminator emits electromagnetic radiation with said proper wavelength;
c) immersing said stamp in said ink, preferably with the aid of an ink pad;
d) running said stamp on said surface area and impressing a geometric pattern on said area;
e) exposing said area to said electromagnetic radiation with the proper wavelength capable of making said ink visible, wherein said electromagnetic radiation is emitted by said illuminator, which is preferably at least one LED supported by spectacles worn by the operator;
f) viewing the pattern traced by said marker on said surface area by said operator.

In a preferred embodiment, said surface area is the skin of a mammal, preferably is the skin of a person.

The surface area marking method of the present invention can be applied to various sectors, of which the following are listed by way of example only: epilation, hair removal, treatment of telangiectasia, erythrosis, red and blue capillaries, angiomas, varicose veins, removal of tattoos, skin stains, non-ablative or ablative photo rejuvenation, peeling, resurfacing, skin tightening, the dermatologic treatment of skin imperfections to be treated surgically and non-surgically, scars, including post-acne scars, wrinkles, condylomata, fibromas, psoriasis, vitiligo.

It is a further object of the present invention an aesthetic or medical treatment, wherein said method is an aesthetic or medical treatment with electromagnetic, mechanical or electric energy, and comprises:

A. providing an area to be treated, wherein said area is a portion of skin of a subject who wants said treatment;
B. marking a geometric pattern on said area to be treated with an invisible and florescent or photosensitive ink using a kit according to the present invention;
C. exposing an area to a source of electromagnetic radiations with the proper wavelength so as to make said ink visible;
D. exposing an area defined by said marking to a source of electromagnetic, mechanical or electrical energy for said aesthetic or medical treatment;
E. repeating the step in D until said area to be treated delimited by said marking is completely treated.

In an embodiment, the electromagnetic energy source itself for said aesthetic or medical treatment is also the source of electromagnetic radiations with the proper wavelength to make said ink invisible.

In an embodiment, said treatment is a treatment of epilation, or of hair removal, or is a treatment of telangiectasia, erythrosis, red and blue capillaries, angiomas, varicose veins, removal of tattoos, of skin stains, or is a non-ablative or ablative photo rejuvenation treatment, a peeling treatment, a resurfacing treatment or is a dermatologic treatment of skin imperfections to be treated surgically and non-surgically, of scars, including post-acne scars, condylomata, fibromas, psoriasis or vitiligo.

The device of the present invention is particularly advantageous in epilation, but also in the treatment of telangectasias, erythrosis, red and blue capillaries, angiomas, varicose veins, removal of tattoos, skin stains, in non-ablative or ablative photorejuvenation, peeling, resurfacing, dermatologic treatment of skin imperfections to be treated surgically and non-surgically, for example, scars, including post-acne scars, condylomata, fibromas, psoriasis, vitiligo.

The rectangular image in output, made possible by the device described herein, makes the exposure of an entire area to the laser possible in a completely even manner during a single treatment. In fact, the geometry of the image in output allows completely covering the area without the need for undesired and detrimental superimpositions. In order to avoid superimpositions during a single treatment using the state-of-the-art devices providing circular spots, some portions of the same area were inevitably left untreated, with the need to recur to one or more further treatments in successive times, with clear drawbacks.

A further advantage that is found in the solution of the present invention is the even distribution of energy within each single spot. In a circular spot obtained by a circular optical fibre, the distribution of the laser energy of the Gaussian type, with an energy concentration peak at the center of the area. Also, where rectangular spots were obtained starting from circular optical fibres, as in the solutions described by way of comparative purposes, said rectangular spots would anyhow have an uneven energy distribution, but of the Gaussian type. With the use of a rectangular optical fibre as provided for by the device of the present invention, the energy is evenly distributed on the entire spot. This solution allows being able to operate with spots having an even energy in the space, thus avoiding the problems related to the presence of underexposed areas where the efficiency is poor, and overexposed areas with the risk of burns. In order to avoid peak areas, with the circular optical fibres of the state of the art there was the need to decrease the power output, to the detriment of a poor efficiency in the area hit by the peripheral portion of the circular spot. With rectangular fibres, which do not have concentration peaks of the energy emitted, it is possible to increase the source power and operate with an efficient power on the entire spot.

The advantages of the kit and method object of the present invention with respect to the state of the art available alternatives are:

the treatment is safer for the patient because superimpositions are avoided;

the treatment is more effective because repeated treatments are not needed;

the treatment is easier, more accurate and faster.

The invention claimed is:

1. A method of dermocosmetic treatment for skin tissue comprising:

providing an area of the skin tissue to be treated;
providing a handpiece, the handpiece comprising;
an illuminator, configured to illuminate the area of the skin tissue to be treated;
a single core rectangular-shaped optical fiber comprising a proximal end to receive laser light and a distal end to transmit rectangular-shaped laser light to the area of skin tissue to be treated; and
providing two laser treatment sources having different wavelengths, the two laser treatment sources configured to:
(i) emit laser light independently, one of simultaneously or sequentially;
(ii) communicate with the single core rectangular-shaped optical fiber; and
(iii) provide uniform intensity distribution of treatment laser light on the area of the skin tissue to be treated; and the method further comprising the steps of:
activating the illuminator to illuminate the area of the skin tissue to be treated; and
activating the two laser treatment sources to impinge a rectangular-shaped laser light image on a rectangular-shaped area within the area of the skin tissue to be treated, wherein the two laser treatment sources emit laser light independently, one of simultaneously or sequentially.

2. The method of claim 1, further comprising the step of adjusting the size of the laser light produced rectangular-shaped images on the area of the skin tissue.

3. The method of claim 1, the handpiece further comprising one or more sensors, the one or more sensors sensing the position of the handpiece with respect to contact with the skin tissue are to be treated.

4. The method of claim 3, the one or more sensors sensing the position of the one or more sensors over the one or more rectangular-shaped areas and communicating the position to a laser emission control system.

5. The method of claim 4, further comprising the step of the one or more sensors providing synchronization signals to the laser emission control system to activate the two laser light sources when the handpiece is aligned with each one of the one or more rectangular-shaped areas on the area of the skin tissue to be treated.

6. The method of claim 1, wherein the optical fiber comprises a square-shaped core for producing a square-shaped image when activated.

7. The method of claim 1, wherein the two laser light sources are a neodymium-YAG rod and an Alexandrite rod.

8. The method of claim 1, wherein the illuminator comprises one of: a halogen lamp, a LED, a gas neon, or a laser.

9. The method of claim 1, further comprising the steps of activating the illuminator to illuminate additional areas of the skin tissue to be treated and then activating the two laser light sources simultaneously to impinge rectangular-shaped laser light images on said additional areas of the skin tissue.

* * * * *